United States Patent [19]

Lynch et al.

[11] Patent Number: 4,675,034
[45] Date of Patent: Jun. 23, 1987

[54] DUST COLLECTOR

[75] Inventors: Gordon Lynch, Edinburgh; Peter McLuckie, Loanhead; David Mark, Stow; James H. Vincent, Haddington, all of Scotland

[73] Assignee: Coal Industry (Patents) Limited, United Kingdom

[21] Appl. No.: 782,421

[22] Filed: Oct. 1, 1985

[51] Int. Cl.⁴ .............................................. B01D 53/30
[52] U.S. Cl. ...................................... 55/270; 55/504; 73/863.23
[58] Field of Search ...................... 55/270, 504; 73/28, 73/863.23, 863.25

[56] References Cited

U.S. PATENT DOCUMENTS

| | | | |
|---|---|---|---|
| 3,686,835 | 8/1972 | Strange et al. | 55/270 |
| 3,748,905 | 7/1973 | Fletcher et al. | 73/28 |
| 4,178,794 | 12/1979 | Jugle et al. | |
| 4,461,184 | 7/1984 | Gandhi et al. | 73/863.25 |
| 4,544,386 | 10/1985 | Trayford et al. | 55/270 |

FOREIGN PATENT DOCUMENTS

| | | |
|---|---|---|
| 1018596 | 1/1966 | United Kingdom . |
| 1192829 | 5/1970 | United Kingdom . |
| 1225107 | 3/1971 | United Kingdom . |
| 1377093 | 12/1974 | United Kingdom . |
| 857777 | 8/1981 | U.S.S.R. ......... 73/863.23 |

Primary Examiner—Bernard Nozick
Attorney, Agent, or Firm—Stevens, Davis, Miller & Mosher

[57] ABSTRACT

A personal dust sampler, for example to be carried on the lapel of a wearer, has a body part with a gas entry protruding therefrom. The entry has an aspiration efficiency of approximately unity for the gas flow rate of a pump (not shown) which is attachable to an exit from the body. Mounted inside the body is a filter which is removable for examination after a sampling period.

5 Claims, 3 Drawing Figures

DUST COLLECTOR

This invention concerns improvements in dust collection, more particularly it concerns a personal dust sampler suitable for collecting airborne dust in workplaces.

The sampling of airborne dust for environmental health purposes has evolved in a great variety of ways. One method is to try to design a sampler which in calm or moving air has an aspiration efficiency of unity over all the particle aerodynamic diameters found; this can be considered as "true total dust". In the case of personal samplers which are carried by individuals to study the dust to which these individuals are exposed, the performance of the personal sampler can be assessed by comparing directly the mass concentration of each fraction of particle aerodynamic diameter of airborne dust collected by the sampler when mounted on a full-size mannequin exposed to dust in a wind tunnel, with that collected through the mouth of the mannequin. If a collection ratio of about one can be achieved over the whole range of aerodynamic diameters which are inspired by the human body, the sampler can be said to be consistent with the inspirability concept of "total dust".

We refer to our co-pending patent published application (UK No. 2,158,233A) and its U.S. equivalent application Ser. No. 725,500, which introduces the concept of a removable filter unit having a protruding lipped entry. Our earlier application, however, is a static sampler which compensates for the movement of a human by constantly rotating the sampling head. A personal sampler, however, is carried constantly by a user, and thus is exposed to essentially the same conditions as the user.

The present invention provides a personal total dust sampler for assessing total inspirable dust, comprising a sampler body, a lipped gas entry of aspiration efficiency of approximately unity protruding from said sampler body, a removable filter within the body and capable of collecting all the respirable dust particles in a sample of gas passed therethrough, and a gas exit sealably engageable with a gas suction means, whereby a sample of gas containing dust may be drawn through the entry and through the filter to deposit dust thereon. Preferred samplers have a body with an aperture, through which the lipped entry protrudes.

Preferably, the filter is removably mounted within a filter unit which is removable from the body, and the filter unit has a gas exit.

Preferably, the body incorporates a chamber with which the gas exit of the filter unit sealably communicates, the chamber having an exit pipe, to which a gas pump may be attached. Preferably, the body is basically cylindrical in form, with an aperture being central in a planar face thereof. Conveniently, the body has means for attachment to the clothing of or equipment carried by a user; this may comprise a baseplate mounted on the other planar face of a cylindrical sampling head body.

Preferably, the lipped entry protrudes 1-2 mm through the aperture and is cylindrical in form; more preferred embodiments have a bevelled external edge. The entry is conveniently about 15 mm in internal diameter when a conventional battery-powered personal sampler pump capable of operating at a flow rate of 21/min is used. Other dimensions and/or shapes of entry may be found to be desirable in tests, if greater or lesser gas flow rates are used, and routine testing can establish whether a particular size and shape of entry provides the requisite aspiration efficiency at a particular gas flow rate.

Preferably, the filter is in the form of a cassette incorporating the entry and carrying within the cassette the filter medium. Conveniently, the cassette may provide for the replacement of the filter medium. A cassette form of filter permits all the dust which enters to be weighed; if only the filter medium were to be weighed to assess the dust collected, the dust which adheres to the inner walls of the cassette would be neglected, and also there would be a risk of accidental alteration of the dust collected. The filter medium itself is not critical provided it is able to collect all the dust particles in the particular sampling application ("dust" includes particulate and fibrous material of natural or man-made origin); suitable filter media are commercially available.

The sampler may be constructed of suitable materials for the duty to be performed; for example, of aluminium alloy, or of brass for use in underground coal mines.

The invention will now be described with reference to the accompanying drawings, in which.

Figure 2:
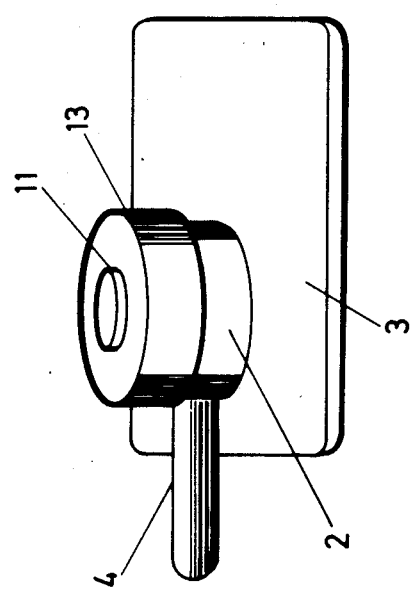
FIG. 2 is a perspective view of the sampler of FIG. 1.
Figure 1:
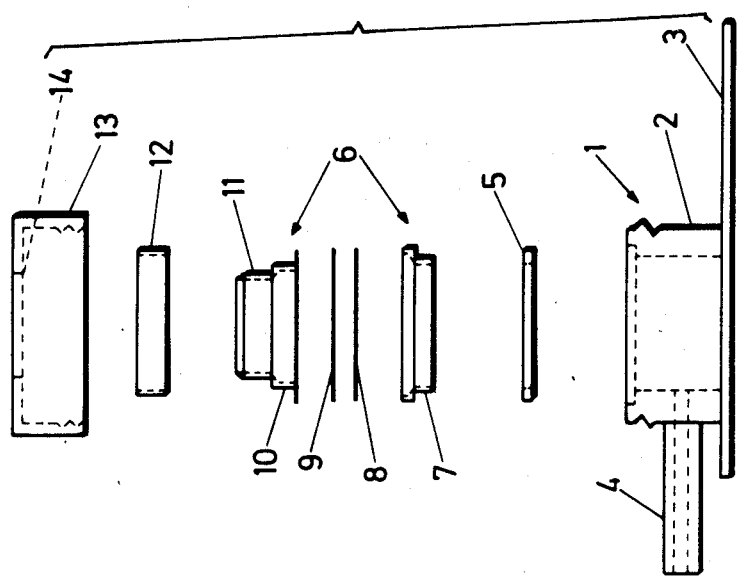
FIG. 1 is an exploded side view of one embodiment of a personal sampler according to the invention.

Referring to FIGS. 1 and 2, the sampler has a body, 1, of a part-threaded cylinder, 2, mounted on a baseplate, 3. A gas exit pipe, 4, connects with the inside of the cylinder. A synthetic rubber O-seal, 5, sits on a shoulder in the top of the cylinder, and sealably engages, in the assembled condition, with the bottom shoulder of a filter cassette, 6. The cassette comprises an annular bottom part, 7, communicating with the inside of cylinder, 2, a filter paper disc, 8, preferably on a fine metal grid support (not shown), a fine PTFE washer, 9, and a cassette top, 10. The cassette may be fitted together in any suitable way, with the cassette top trapping the washer and filter into the bottom part by being a friction fit or by a bayonet lock mechanism or any other suitable method. The cassette top has an upper cylindrical portion, 11, which acts as the lipped entry to the filter cassette.

A PTFE cylinder, 12, sits upon the lower shoulder of the cassette top and transfers pressure from a threaded cap, 13, which engages the thread on the cylinder, 2. The cap has a central aperture, 14, through which extends in the assembled condition, about 1.5 mm of the lipped entry, 11. As cap 13 is screwed down, suitably only finger-tight, onto the body of the sampler the cassette top is pressed into sealing engagement with the PFTE washer 9, and the cassette bottom part 7 is pressed into sealing engagement with the O-seal, 5, and the body of the sampler.

In use, a filter cassette is pre-weighed under standard conditions, and, if necessary, stored in a sealed and numbered tin or the like. A sampler is assembled and fitted onto the lapel of a user, so that the lipped entry faces outwards, and a standard personal sampler pump (not shown) is attached to gas exit pipe 4. At the end of the shift, or other predetermined sampling time, the sampler may be disassembled, and the cassette re-weighed. In this embodiment of the sampler of the invention, all the dust collected within the filter cassette is to be considered as total inspirable dust and therefore is included in the total weight of dust. If desired, the dust deposited on the internal walls may be recovered by washing or brushing out and subjected to more detailed study.

Figure 3:
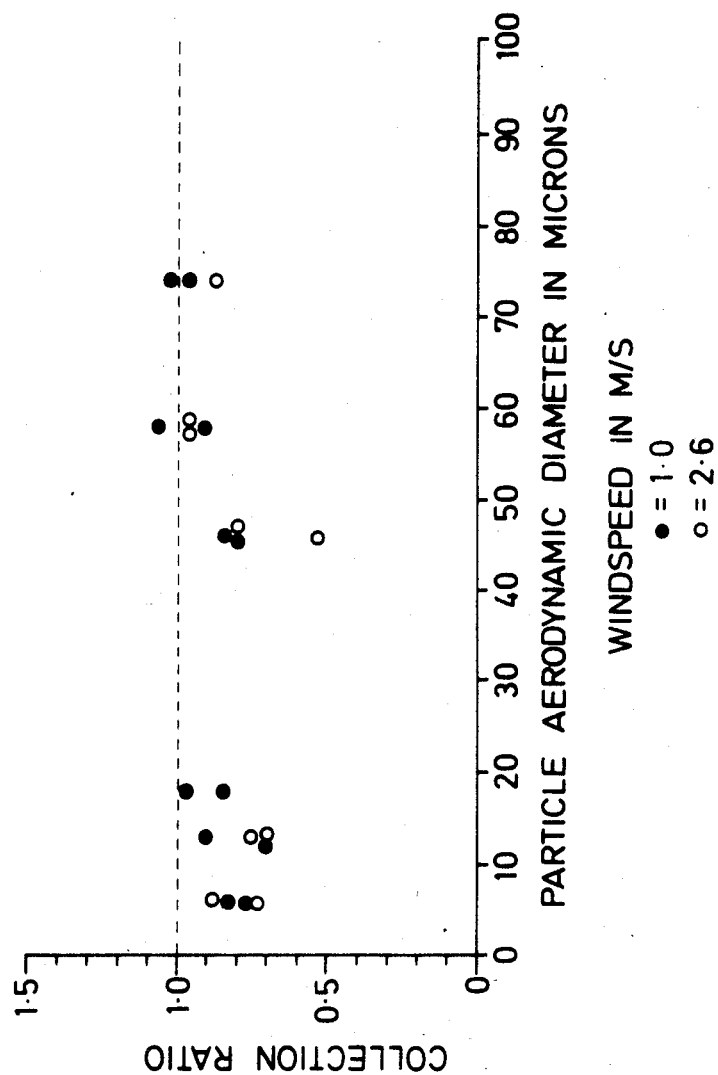
FIG. 3 is a plot of collection ratio against dust particle aerodynamic diameter in microns for different wind speeds in a test wind tunnel, for the sampler of FIGS. 1 and 2.

Referring to FIG. 3, it can be seen that the prototype sampler shows an average collection ratio over a wide particle size range, which is close to the unity value of an ideal personal sampler. It is not believed that any known personal sampler is capable of equivalent results, and generally existing commercial samplers show considerable variation from the unity value, especially at larger particle sizes.

We claim:

1. A personal dust sampler comprising a sampler body having an entry aperture exposed to ambient air and an air exit sealably attachable to pump means, a removable filter cassette mounted with the body and means for removably holding it in position, said filter cassette having an internal filter and comprises an entry for air which may be contaminated with dust, said entry having a cylindrical upstanding wall open to the air at one end and communicating with a first side of the internal filter at the other end; a cassette air exit communicating with the other side of the internal filter and sealably connecting with the air exit of the sampler body, said cylindrical upstanding wall of the cassette air entry protruding through the entry aperture to form a lip cooperating with the sampler body to provide an aspiration efficiency with respect to dust of approximately unity.

* * * * *